United States Patent
D'Arcy et al.

(10) Patent No.: US 12,290,372 B2
(45) Date of Patent: May 6, 2025

(54) SYSTEM AND METHOD FOR AUTOMATIC EVOKED POTENTIAL MEASUREMENT

(71) Applicant: Health Tech Connex Inc., Surrey (CA)

(72) Inventors: Ryan Clarke Newell D'Arcy, North Vancouver (CA); Fabio Bollinger, Langley (CA); Shaun Dean Fickling, Coquitlam (CA); Zachary Frehlick, Vancouver (CA); Sujoy Ghosh Hajra, Ottawa (CA); Sunny Gurm, Burnaby (CA); Nazanin Hamzei, Vancouver (CA); Caressa Chang Liu, North York (CA); Ashley Candice Livingstone, Coquitlam (CA); Christopher James Smith, Abbotsford (CA); Pamela Tannouri, Burnaby (CA); Mike Thiem, Calgary (CA); Evangeline Yee, Coquitlam (CA); Shaquile Ryan Nijjer, Surrey (CA)

(73) Assignee: HEALTH TECH CONNEX INC., Surrey (CA)

( * ) Notice: Subject to any disclaimer, the term of this patent is extended or adjusted under 35 U.S.C. 154(b) by 793 days.

(21) Appl. No.: 17/440,718

(22) PCT Filed: Mar. 18, 2020

(86) PCT No.: PCT/CA2020/050360
§ 371 (c)(1),
(2) Date: Sep. 17, 2021

(87) PCT Pub. No.: WO2020/186353
PCT Pub. Date: Sep. 24, 2020

(65) Prior Publication Data
US 2022/0167908 A1 Jun. 2, 2022

Related U.S. Application Data

(60) Provisional application No. 62/820,173, filed on Mar. 18, 2019.

(51) Int. Cl.
*A61B 5/377* (2021.01)
*A61B 5/00* (2006.01)
(Continued)

(52) U.S. Cl.
CPC .............. *A61B 5/377* (2021.01); *A61B 5/301* (2021.01); *A61B 5/398* (2021.01); *A61B 5/726* (2013.01)

(58) Field of Classification Search
CPC ........... A61B 5/301; A61B 5/31; A61B 5/377; A61B 5/398; A61B 5/725; A61B 5/726
See application file for complete search history.

(56) References Cited

U.S. PATENT DOCUMENTS

| | | | |
|---|---|---|---|
| 5,230,344 A | 7/1993 | Ozdamar et al. | |
| 5,243,517 A * | 9/1993 | Schmidt | A61B 5/377 434/236 |

(Continued)

FOREIGN PATENT DOCUMENTS

DE 10339680 A1 3/2005

OTHER PUBLICATIONS

D'Arcy et al., Towards Brain First-Aid: A Diagnostic Device for Conscious Awareness, IEEE Transactions on Biomedical Engineering, Mar. 3, 2011, pp. 750-754, vol. 58, Issue No. 3., IEEE Institue of Electrical and Electronics Engineers, https://ieeexplore.ieee.org/abstract/document/5625897.

(Continued)

*Primary Examiner* — Daniel L Cerioni
*Assistant Examiner* — Abel Seifu Abegaz
(74) *Attorney, Agent, or Firm* — McCarthy Tétrault LLP

(57) ABSTRACT

A system and method is operable to automatically determine the amplitude and latency of one or more evoked potential (EP) or event-related potential (ERP) from electroencephalography (EEG) data. The EEG data from an EEG scan is
(Continued)

separated into one or more epochs containing the desired EP or ERP waveforms. Epochs corresponding to the same type of EP or ERP such as N100, P300, and N400 are averaged automatically. The averaged epochs are automatically filtered in the time-frequency domain using an automatically selected filtering mask associated with the type of EP or ERP. A corresponding peak is automatically identified from the filtered epoch, in which the amplitude and latency is automatically measured.

24 Claims, 8 Drawing Sheets

(51) Int. Cl.
  *A61B 5/301* (2021.01)
  *A61B 5/398* (2021.01)

(56) References Cited

U.S. PATENT DOCUMENTS

| | | | |
|---|---|---|---|
| 5,792,069 A * | 8/1998 | Greenwald | A61B 5/369 607/45 |
| 9,339,227 B2 | 5/2016 | D'arcy et al. | |
| 2003/0144601 A1 * | 7/2003 | Prichep | A61B 5/369 600/544 |
| 2007/0191727 A1 | 8/2007 | Fadem | |
| 2011/0224570 A1 | 9/2011 | Causevic | |
| 2013/0245422 A1 * | 9/2013 | D'arcy | A61B 5/7246 600/409 |
| 2014/0324118 A1 | 10/2014 | Simon et al. | |
| 2020/0012346 A1 * | 1/2020 | Schiff | A61B 5/383 |
| 2020/0015696 A1 | 1/2020 | Connolly et al. | |
| 2020/0178849 A1 * | 6/2020 | Cheng | A61B 5/112 |

OTHER PUBLICATIONS

Davis et al., Stimulus Onset Hub: an Open-Source, Low Latency, and Opto-Isolated Trigger Box for Neuroscientific Research Replicability and Beyond, Frontiers in Neuroinformatics, www.frontiersin.org, Feb. 6, 2020, pp. 1-9, vol. 14, Article 2, https://doi.org/10.3389/fninf.2020.00002.

Fleck-Prediger et al., Point-of-care brain injury evaluation of conscious awareness: wide scale deployment of portable HCS EEG evaluation, Neuroscience of Consciousness, Nov. 23, 2018, pp. 1-12, vol. 2018, Issue 1, niy011, Oxford University Press, https://academic.oup.com/nc/article/2018/1/niy011/5205809.

Ghosh Hajra et al., Developing Brain Vital Signs: Initial Framework for Monitoring Brain Function Changes Over Time, Frontiers in Neuroscience, www.frontiersin.org, May 12, 2016, pp. 1-10, vol. 10, Article 211, https://doi.org/10.3389/fnins.2016.00211.

Ghosh Hajra et al., Multimodal characterization of the semantic N400 response within a rapid evaluation brain vital sign framework, Journal of Transactional Medicine, https://translational-medicine.biomedcentral.com/, Jun. 4, 2018, pp. 1-11, vol. 16, Article 151, https://doi.org/10.1186/s12967-018-1527-2.

Mayhew et al., Automated single-trial measurement of amplitude and latency of laser-evoked potentials (LEPs) using multiple linear regression, Clinical Neurophysiology, Apr. 27, 2006, pp. 1331-1344, vol. 117.

Quiroga et al., Single-trial event-related potentials with wavelet denoising, Clinical Neurophysiology, Feb. 2003, pp. 376-390, vol. 114, Issue 2, https://doi.org/10.1016/S1388-2457(02)00365-6.

Walbran et al., Spike detection in the preterm fetal sheep EEG using Haar wavelet analysis, 33rd Annual International Conference of the IEEE EMBS, Sep. 3, 2011, pp. 7063-7066.

Jacquin Arnaud et al., Optimal Denoising of Brainstem Auditory Evoked Response (BAER) for Automatic Peak Identification and Brainstem Assessment, Conference Proceedings Annual International Conference of the IEEE Engineering in Medicine and Biology Society, Aug. 30, 2006, pp. 1723-1726, DOI: 10.1109/IEMBS.2006.259785, New York, USA.

Markazi Seyedehmina Ayoubian et al., Wavelet Filtering of the P300 Component in Event-Related Potentials, Annual International Conference of the IEEE Engineering in Medicine and Biology Society, Aug. 30, 2006, pp. 1719-1722, DOI: 10.1109/IEMBS.2006.260691, New York, USA.

Centerspace Software, Filtering with Wavelet Transforms, Dec. 18, 2015, retrieved from https://www.centerspace.net/wavelet-transforms on Oct. 25, 2022.

Gratton Gabriele et al., A New Method for off-line removal of ocular artifact, Electroencephalography and Clinical Neurophysiology, Apr. 1, 1983, pp. 468-484, vol. 55, Issue 4, Elsevier, Netherlands.

Warbrick T et al., Single-trial P3 amplitude and latency informed event-related fMRI models yield different Bold response patterns to a target detection task, Neuroimage, Jun. 6, 2009, pp. 1532-1544, vol. 47, Issue 4, Elsevier, Amsterdam, Netherlands.

Van Hooff Hannie, Analysis of Event Related Potentials: Step by Step, May 7, 2017, pp. 1-13, retrieved from http://eegget-it.n./erp_analysis.html on Oct. 25, 2022.

* cited by examiner

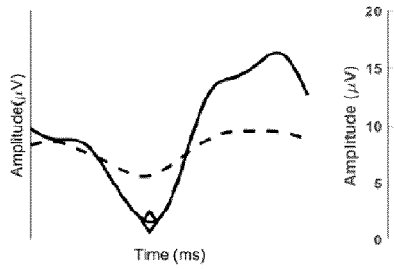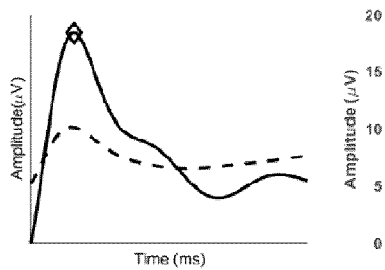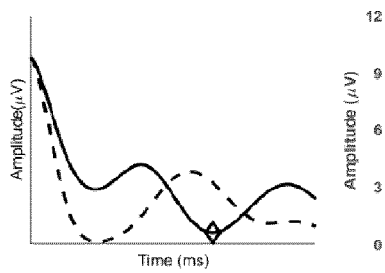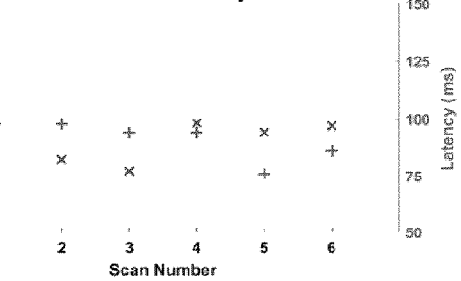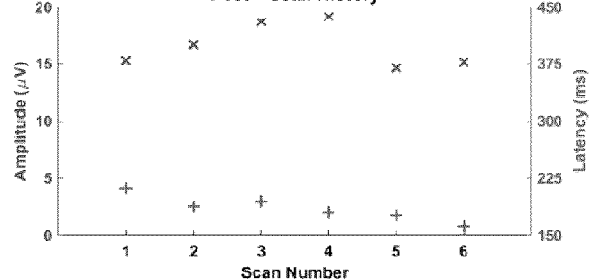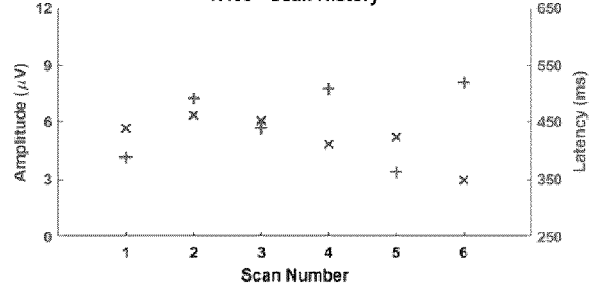
FIG. 8

SYSTEM AND METHOD FOR AUTOMATIC EVOKED POTENTIAL MEASUREMENT

RELATED APPLICATIONS

This application claims priority from U.S. Provisional Patent Application No. 62/820,173 filed Mar. 18, 2019 entitled SYSTEM AND METHOD FOR AUTOMATIC EVOKED POTENTIAL MEASUREMENT. For the purposes of the United States, this application claims the benefit under 35 USC § 119 of U.S. Provisional Patent Application No. 62/820,173 filed Mar. 18, 2019 entitled SYSTEM AND METHOD FOR AUTOMATIC EVOKED POTENTIAL MEASUREMENT which is incorporated herein by reference in its entirety.

TECHNICAL FIELD

The present disclosure relates generally to acquiring and processing electrical signals, and more particularly to a system and method for automatically recording and quantifying waveforms from devices/techniques including evoked potential (EP) and/or event-related potential (ERP) obtained from electroencephalography (EEG) measurements.

BACKGROUND

Electroencephalography (EEG) is a non-invasive, electrophysiological method of monitoring brain activity, using multiple electrodes placed on the scalp to measure voltage fluctuations resulting from ionic current within neurons of the brain. EEG can be used to measure evoked neural responses ranging from lower level sensory processing (often called evoked potentials, or "EPs") to higher level cognitive processing (often called event-related potentials, or "ERPs"). EPs and ERPs can generally be measured through signal averaging to isolate specific electrical potential activity associated with the presentation of a series of stimuli. The study of EPs and ERPs provides a measure of processing between a stimulus and response and is recognized as a well-established quantitative application of EEG. Importantly, these neural responses provide objective, quantifiable information across a spectrum of brain functions. They are sensitive to various states of brain dysfunction with established test-retest reliability, making them a suitable and empirically-validated non-invasive measure of brain physiology in health, injury, and disease states.

EPs and ERPs provide complex information about brain processing and are subject to numerous sources of noise, which limit measurement repeatability and reliability outside of a controlled laboratory setting. Solutions to this problem within academia have often been reliant on experimental design recommendations and a set of standard signal processing techniques designed to reduce or eliminate such sources of noise. These solutions, while important and useful, have not overcome certain barriers to enable routine measurement of EPs and/or ERPs as indicators of brain health in clinical and related environments.

Typical experimental design parameters for measuring EPs and/or ERPs using EEG involve extended data collection sessions with long inter-stimulus intervals to provide a stable baseline activity period prior to the onset of each stimulus. Furthermore, a large number of stimulus repetitions are generally used to enable trial averaging to improve EP/ERP signal-to-noise ratio. These protocols may result in lengthy (typically around an hour) recording sessions to collect sufficient EP/ERP data for a specific response. To collect a number of different responses, the length of the recording session is often consequently extended, as dependent on the number of trials per response and the number of different responses.

Using the above-described design parameters, signal processing algorithms can be applied to the collected EEG data to produce stable and interpretable EP/ERP waveforms (for example, U.S. Pat. No. 9,339,227 to D'arcy et al., and D'Arcy, Ryan C N, et al., "Towards brain first-aid: a diagnostic device for conscious awareness" *IEEE transactions on biomedical engineering* 58.3 (2010): 750-754. disclose a method and system to capture EEG data to identify EP/ERP features). Pre-processing of EEG data has been disclosed to enhance signal-to-noise ratios (SNR) in Fleck-Prediger, Carolyn M., et al. "Point-of-care brain injury evaluation of conscious awareness: wide scale deployment of portable HCS EEG evaluation" *Neuroscience of consciousness* 2018.1 (2018): niy011.

However, human intervention is still required in the form of user-supplied input from a trained expert. Specifically, one major processing step that typically requires human input is peak identification and selection from the EP/ERP waveforms. The requirement for human review often makes the EP/ERP capture and review process labour-intensive and time-consuming. Manual review furthermore adds a user-dependent limitation, which fundamentally limits objective, repeatable, accessible, and standardized results thereby generally precluding these processes from use in clinical applications.

As such, there is a need for solutions for addressing or ameliorating at least some of the problems identified above.

SUMMARY OF THE DISCLOSURE

In general, the present specification describes a system and method for recording and quantifying EP/ERP waveforms obtained from EEG measurements in a fast, repeatable and automated manner.

One aspect of the invention provides a computer-implemented method to automatically measure an amplitude and a latency of at least one evoked potential (EP) and/or event-related potential (ERP) from electroencephalography (EEG) data. The automation method includes: (a) separating the EEG data into at least one epoch, each epoch containing an ERP waveform associated with at least one type of ERP. The method also includes: (b) upon automatically grouping each epoch according to ERP type, and for each type of EP/ERP having at least one associated epoch, automatically processing the at least one associated epoch by: computing, automatically, an average of the at least one associated epoch to output an averaged epoch; upon detecting the outputted average epoch, outputting a time-frequency domain representation of the averaged epoch; automatically applying a time-frequency mask to the time-frequency representation of the averaged epoch to output a masked epoch wherein the time-frequency mask is automatically selected from a set of time-frequency masks configured to reject at least one time-frequency component of the time-frequency representation of the averaged epoch; outputting, automatically upon detecting an outputted masked epoch, a filtered epoch corresponding to a time domain representation of the masked epoch; automatically selecting a position in the filtered epoch corresponding to an EP/ERP waveform peak; and automatically determining an amplitude value and a latency value of the EP/ERP waveform peak.

Step (a) of separating the EEG data into at least one epoch is performed automatically. In step (b), the operations are performed automatically for each type of EP/ERP having at least one associated epoch. In particular embodiments, automatically selecting a position in the filtered epoch and determining an amplitude value and a latency value are performed using automatic peak detection.

In some embodiments, the automation method includes automatically filtering the EEG data before separating the EEG data into the at least one epoch. The filter that is used may be a bandpass filter.

According to some embodiments, the automation method includes filtering the EEG data using automatically retrieved electrooculography (EOG) data associated with the EEG data, wherein the EEG data is automatically filtered using the EOG data as a reference signal to automatically remove EEG data artifacts resulting from ocular activity.

The automation method may include automatically excluding an epoch of the at least one associated epoch from computation of the averaged epoch when an EEG voltage within that epoch is determined, automatically, to exceed a voltage threshold value.

For each of the at least one associated epoch, the automation method may include automatically computing a corresponding mean value from that associated epoch and automatically subtracting the mean value from that associated epoch prior to computing the averaged epoch.

In particular embodiments, the time-frequency domain representation is automatically obtained by applying a wavelet transform to the averaged epoch. The filtered epoch may be obtained by applying an inverse wavelet transform to the masked epoch. The wavelet transform may be automatically selected from one of a Haar wavelet, Daubechies wavelet, Biothogonal wavelet, Coiflets wavelet, Morlet wavelet, Symlets wavelet, Mexican Hat wavelet, and Meyer wavelet.

In some embodiments, the time-frequency mask is pre-defined for each EP/ERP type, and the time-frequency mask is based on at least one EP/ERP waveform of the same EP/ERP type selected from a normative database. In other embodiments, the time-frequency mask for each EP/ERP type of the at least one type of EP/ERP is dynamically generated based on signal properties of the EP/ERP waveform.

The EP/ERP waveform peak may correspond to a waveform feature of the filtered epoch. The waveform feature may be automatically identified within a time window of interest (TOI) applied to the filtered epoch, based on a pre-defined time interval determined based on a known latency range for a given type of EP/ERP.

Another aspect of the invention is directed to an automated electroencephalography (EEG) system. The system includes an acquisition hardware interface to automatically acquire EEG data by receiving at least one EEG signal from at least one EEG electrode, a data storage subsystem to automatically store the EEG data in at least one EEG data file, and a data processing module operable to automatically process the EEG data in the at least one EEG data file to automatically measure an amplitude and a latency of at least one evoked response potential (EP/ERP). The data processing module is operable to process the EEG data by: (i) separating the EEG data into at least one epoch, each epoch containing an EP/ERP waveform associated with at least one type of EP/ERP. The data processing module is also operable to process the EEG data by: (ii) upon automatically grouping each epoch according to EP/ERP type, and for each type of EP/ERP having at least one associated epoch, automatically processing the at least one associated epoch by: computing, automatically, an average of the at least one associated epoch to output an averaged epoch; upon detecting the outputted average epoch, automatically outputting a time-frequency domain representation of the averaged epoch; automatically applying a time-frequency mask to the time-frequency representation of the averaged epoch to output a masked epoch wherein the mask is automatically selected from a set of time-frequency masks configured to reject at least one time-frequency component of the time-frequency representation of the averaged epoch; outputting, automatically upon detecting an outputted masked epoch, a filtered epoch corresponding to a time domain representation of the masked epoch; automatically selecting a position in the filtered epoch corresponding to an EP/ERP waveform peak, and automatically determining an amplitude value and a latency value of the EP/ERP waveform peak.

Additional aspects of the present invention will be apparent in view of the description that follows.

BRIEF DESCRIPTION OF THE DRAWINGS

Features and advantages of the embodiments of the present invention will become apparent from the following detailed description, taken with reference to the appended drawings in which:

FIG. 8 is an example scan report showing EP/ERP amplitude and latency for N100, P300, and N400 ERP.

DETAILED DESCRIPTION

Figure 1:
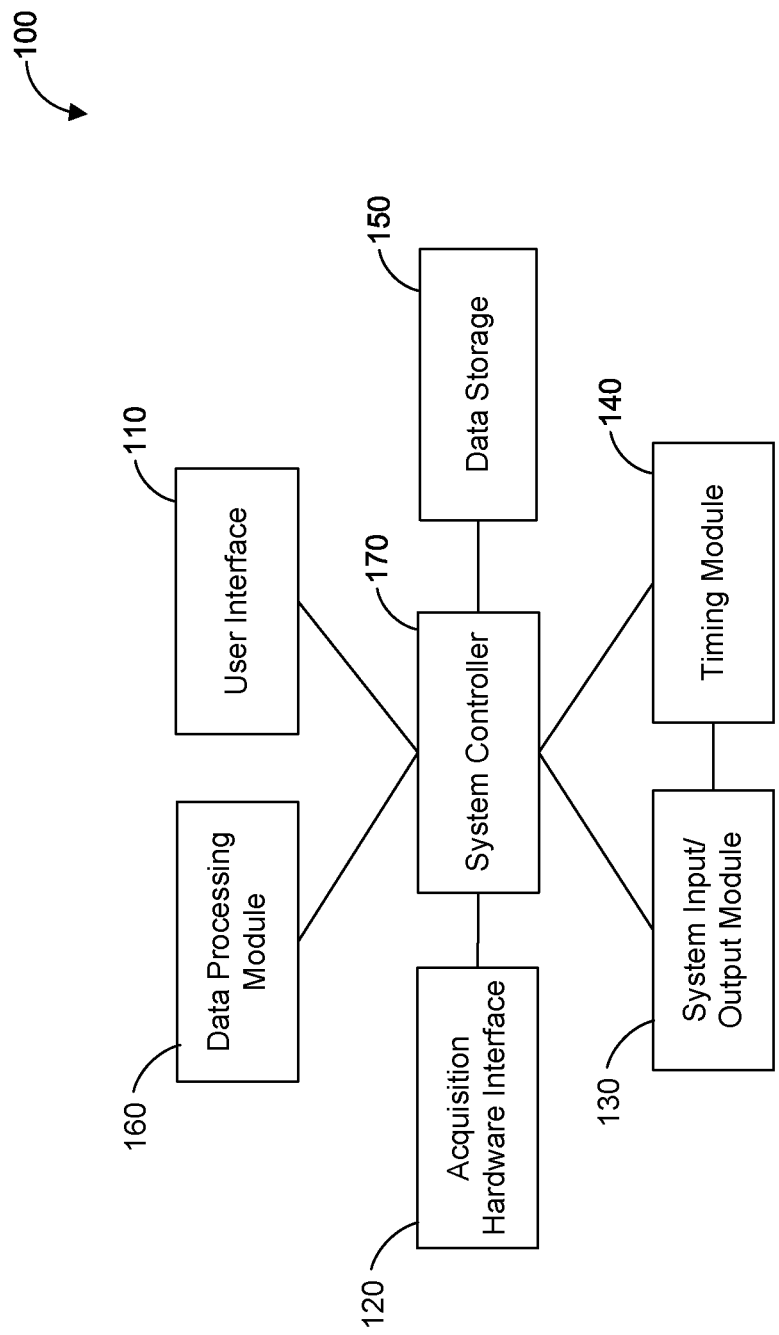
FIG. 1 is a block diagram of an EP/ERP system.

The description that follows, and the embodiments described therein, are provided by way of illustration of examples of particular embodiments of the principles of the present invention. These examples are provided for the purposes of explanation, and not limitation, of those principles and of the invention.

Evoked potentials/event-related potentials (EPs/ERPs) can be measured using any electroencephalography (EEG) system with an appropriate device configuration. In view of the foregoing, EP/ERP responses can be used as an indicator of a human or non-human animal's brain health. Accordingly, well-established responses can be translated into "brain vital signs" according to a framework disclosed by Ghosh Hajra S., Liu C. C., Song X., Fickling S. D., Liu L. E., Pawlowski G., et al., "Developing brain vital signs: Initial framework for monitoring brain function changes over time. Front. Neurosci. 2016; 10: 1-10, and by Ghosh Hajra S, Liu C C, Song X, Fickling S D, Cheung T P L, D'Arcy R C N. "Multimodal characterization of the semantic N400 response within a rapid evaluation brain vital sign framework". J. Transl. Med. 2018; 16: 151, the entirety of which are hereby incorporated by reference. To monitor brain function, EP/ERP changes can be detected by way of analyzing corresponding EP/ERP waveforms over a period of time. The brain vital signs framework preserves essential EP/ERP results and incorporates a normative comparison framework analogous to existing vital sign metrics for heart rate and blood pressure. The study of brain vital signs can be used to evaluate, diagnose, assess and monitor brain injuries and/or diseases such as concussion-related brain injuries, age-related cognitive impairment, dementia, stroke, migraines, epilepsy, developmental disorders/diseases, brain trauma, Parkinson's disease, multiple sclerosis, encephalopathies and the like.

One approach to assessment of brain vital signs uses six measures of ERP responses representing auditory sensation (N100), basic attention (P300), and cognitive processing (N400). The brain vital signs framework further includes normative evaluations of corresponding ERP amplitudes and latencies metrics for each of the three responses. ERP responses within the brain vital signs framework can be generated using a brief (<10 minute) auditory stimulus sequence comprising interlaced tones and spoken word-pair primes. Auditory tones can be randomly distributed into, for example, 70-90% standard tones and 10-30% deviant tones conditions, to evoke the N100 and P300 ERPs. The N400 ERP can be obtained from word pair primes that are either semantically congruent (e.g., bread-butter) or incongruent (e.g., bread-window). Brain vital sign scores can be generated based on the measured ERP amplitudes and latencies and compared to scores or ranges of scores known to be associated with normal or atypical brain function.

As noted previously, conventional EP/ERP acquisition and analysis methods are time consuming and generally restricted to controlled laboratory settings. As such, there is a desire to automate the EP/ERP acquisition and analysis, including the steps of peak identification and selection, which are required to quantify response amplitude and latency. However, even when the EEG waveforms are processed with existing state-of-the-art signal processing techniques, waveform variability and noise has so far only allowed the step of peak identification and selection to be a semi-automated process. That is, peak identification and selection still requires human expert input. In practice, there may be multiple apparent peaks within the expected time range of a particular EP/ERP component. The origins of the peaks may be a result of a brain response (i.e. the EP/ERP of interest) or signal artifacts caused by internal and/or external noise (e.g. blinking, movement, alpha, et cetera). Expert knowledge is therefore necessary to accurately choose between these "candidate" peaks. The challenge in automating the peak identification and selection process is therefore being able to automatically discriminate between candidate peaks and selecting the peak, if present, that corresponds to the EP/ERP of interest.

Existing systems and methods have shown that measurement time can be shortened by reducing inter-trial timing, recording fewer trials, and interleaving different stimulus types to create an integrated stimulation protocol of a defined length (e.g. in the range of 5-10 minutes). However, imposing these conditions of data collection is likely to aggravate certain existing sources of noise or introduce new sources of noise (for example, inter-trial signal contamination and variations in subject attention). Such conditions thereby further increase the difficulty of automating the peak identification and selection process. Therefore, shortened and fully automated data collection protocols would require novel methods utilizing improved signal processing techniques to fully remove the requirement for review by human experts.

Disclosed herein is an automated system to implement EP/ERP acquisition and processing at a large scale that is commensurate with the realistic demands of clinical environments. More specifically, the disclosed EP/ERP system is intended to acquire the EPs and/or ERPs of interest within a desired time period and automate the waveform processing to meet the time constraints and processing requirements demanded in clinical applications. The measured EPs and/or ERPs may be used for direct evaluation of brain function and brain function changes, or for use within the brain vital signs framework described above. For the purposes of the present disclosure, the terms "EP" and "ERP" are used interchangeably to refer to one or more electrical potentials measured from the nervous system of a human or non-human animal following an applied stimulus, using EEG and/or other time varying recording systems or techniques used in functional brain imaging. It is further noted that EP/ERPs and EEG are intended as the representative demonstration, as the concepts disclosed may be applicable to a plurality of brain devices/techniques capable of measuring any time-varying signals associated with brain activity such as magnetoencephalography, near infrared spectroscopy, functional magnetic resonance imaging, and the like.

Referring first to FIG. 1, shown therein is a block diagram of an EP system 100 operable to acquire and process EP/ERP waveforms and to automatically output amplitude and latency measurements with a high level of accuracy and repeatability. In the present embodiment, EP system 100 interfaces with data acquisition components for acquiring EEG signals from a human or animal subject. EP system 100 includes data processing components for identifying EP/ERP waveforms from the acquired EEG signals and measuring the associated amplitude and latency.

In some embodiments, EP system 100 can be implemented using a general purpose computing device. The general purpose computing device may be configured to communicate with suitable EEG hardware and/or electrooculography (EOG) hardware to acquire EEG and/or EOG signals suitable for quantifying EP/ERP waveforms. EP system 100 can incorporate other sources of data, such as heart rate, light, movement, and the like. The computing device may take various forms, including but not limited to, desktop computers, laptop computers, cloud-based servers, and mobile computing devices such as tablets, smartphones, and other portable devices. In another embodiment, EP system 100 can be implemented as a standalone device configured and/or programmed specifically to provide functionalities described herein. A description of the various components of EP system 100 is now presented.

EP system 100 includes a user interface 110 that can be presented as a graphical user interface on a display screen for a user to control the various aspects of an EEG data acquisition or "scan" session and to review the status of EP system 100. For example, input controls (e.g. on-screen keyboard or physical keyboard) can be provided to allow parameters of the scan session to be entered. Parameters can include contextual information such as the name of the subject and the location of the scan session. User interface 110 can further be used to select a pre-defined stimulus sequence for the scan. Alternatively, user interface 110 may be used to allow the user to specify a customized scan sequence.

During a scan, user interface 110 is operable to indicate scan progress and/or indicate whether errors have been detected by EP system 100 that would affect the collection or quality of the scanned data. For example, a scan may not proceed if the EEG hardware is not responsive or where EEG electrode impedance levels are outside of a threshold value or range. After the scan, the user can use user interface 110 to save scan data and/or scan reports to data storage 150 for retrieval and review at a later time.

Acquisition hardware interface 120 is operable to establish a communication link between EP system 100 and EEG hardware for collecting EEG signals from at least one EEG electrode. The communication link can be established through any method known to those in the art, including, but not limited to wired interfaces, wireless interfaces, or a combination of wired and wireless interfaces. The status of the communication link can be indicated in user interface 110 to indicate whether or not the link is active. For example, an indicator in user interface 110 may use a green indicator to show that the link is active and a red indicator to show that the link is inactive. In some embodiments, acquisition hardware interface 120 further includes an interface for communicating with EOG hardware for the measurement of a subject's ocular activity (e.g. eye movements and blinking) using electrodes placed above and beside the eye socket of the subject. In other embodiments, the EOG measurement can be inferred from other electrodes using machine learning models. Acquisition hardware interface 120 may be operable to scan for available EEG and/or EOG hardware equipment intended for use with EP system 100 and select the proper communication protocol to establish a communication link therewith.

EEG electrode impedance may affect the quality of the resulting EEG signal, and therefore, may have an impact on the ability to reliably perform peak identification and selection of the corresponding EP waveform. As such, in some embodiments, acquisition hardware interface 120 may also be operable to gather impedance measurements from the EEG hardware. For example, system controller 170 may periodically poll (e.g. on demand or at a pre-determined polling frequency) the EEG hardware via acquisition hardware interface 120 for impedance measurements. The gathered impedance values can be displayed in user interface 110. For example, user interface 110 may graphically indicate electrode impedance using a colour map to indicate impedance quality or display a schematic diagram of electrode locations with impedance indicators.

System input/output module 130 is operable to handle system input and output tasks for EP system 100. For example, user interface 110 is used to present information and receive data input from a user in which the corresponding inputs entered via the user interface 110 are handled by system input/output module 130 by relaying input data to other modules or performing actions in response to received inputs. Inputs can include user input from an input device such as a switch, button, mouse, keyboard, touch screen, and the like, or data input from data storage 150. Output can include graphical images for display on a display screen or stimulus sequences for the purpose of evoking a measurable response from the subject. For example, a stimulus in a sequence can be an audio signal corresponding to an audio tone or audible spoken word pair to elicit the desired N100, P300, and N400 responses. The output audio may be pre-recorded and saved as audio files in data storage 150 or generated dynamically by system input/output module 130 using audio synthesis or speech synthesis techniques known to those in the art. For output of pre-recorded audio, system input/output module 130 is operable to obtain the appropriate audio sequence for the scan by assembling the appropriate audio files of pre-recorded tones or words retrieved from data storage 150.

Timing module 140 is operable to control the timing of stimulus output during a scan session by ensuring that an appropriate time delay is applied between stimuli (e.g. tone-type or word-type stimuli) within a stimulus sequence. A sequence used in a scan session generally includes a combination of tone-type and word-type stimuli, in which the timing delay can vary depending on the type of stimulus outputted. For example, in some embodiments, a delay between 500 ms and 600 ms can be imposed by timing module 140 after onset of a tone-type stimulus. On the other hand, the timing delay after onset of a word-type stimulus can be greater than the delay for a tone-type stimulus, between 1400 ms and 1500 ms.

Data storage 150 is operable to store information and data used by EP system 100 such as configuration files and data files corresponding to the various stimuli for output. Data storage 150 is further operable to store scan session data such as raw and processed EEG and/or EOG data and related reports. Data storage 150 can be implemented in a manner known to those in the art. For example, data storage 150 may be a magnetic or optical disk drive, solid state drive, networked disk drive, distributed storage resource (e.g. cloud-based storage), database, and the like.

Data processing module 160 is operable to process the acquired EEG and/or EOG signals to automatically identify EP/ERP waveforms of interest, perform peak identification and selection, and determine corresponding amplitudes and latencies of the EP/ERP waveforms. In some embodiments, data processing module 160 may also be used to provide processing power to other elements of EP system 100. For example, data processing module 160 can be triggered by system input/output module 130 to synthesize audio for the stimulus sequence. In another example, user interface 110 may use data processing module 160 to render the necessary graphical elements for display.

Figure 2:
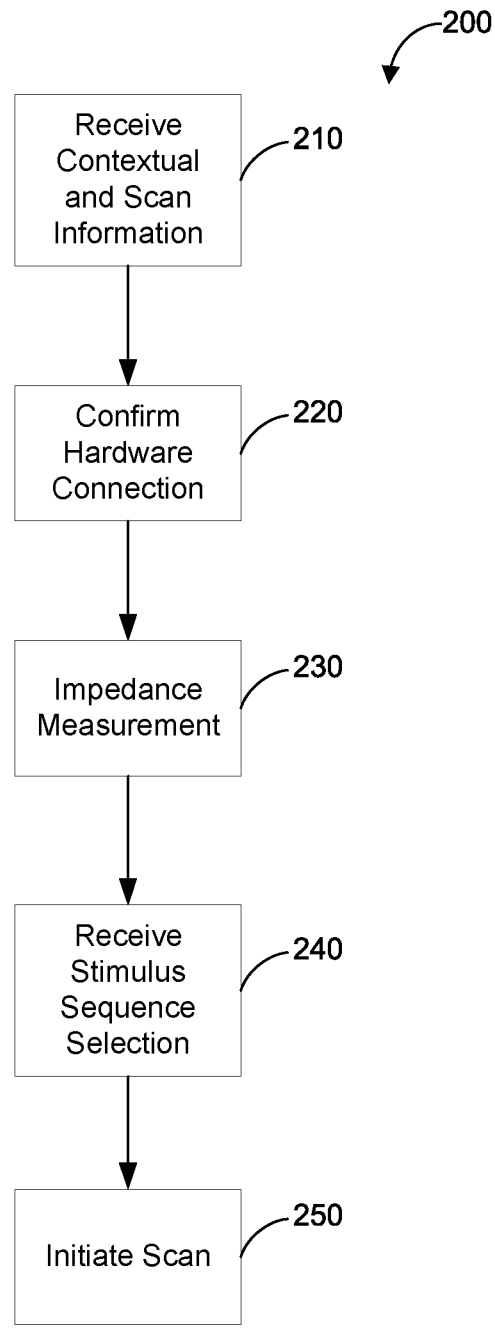
FIG. 2 is a flowchart of a procedure for carrying out an EEG scan using the EP/ERP system of FIG. 1.

System controller 170 is operable to coordinate the operation of EP system 100, including acquisition of EEG and/or EOG data and processing of such data. FIG. 2 shows a flowchart illustrating an exemplary method 200 that may be carried out by system controller 170 to conduct a scan. In some embodiments, the system controller can be implemented by way of a computerized process that oversees one or more aspects of the operation of EP system 100 and/or one or more steps of exemplary method 200. For example, a computerized process may control the polling frequency of acquisition hardware interface 120 to ensure compliance with electrode impedances (as explained in more detail below). In other embodiments, the system controller 170 may include user input to oversee one or more aspects of the operation of EP system 100 and/or one or more steps of exemplary method 200. For example, the system controller may receive input from a user to open an appropriate data processing suite and manually process a data file from data storage 150. In yet other embodiments, user input is required to coordinate the operation of EP system 100 and/or the steps of exemplary method 200.

Referring to FIG. 2, at step 210 of method 200 contextual information (e.g. clinic information and location of the scan) as described previously and scan information (e.g. identifier of the subject, the run number) is received. Such information may be inputted by the user, for example, via user interface 110.

At step 220, an active communication link with the EEG and/or EOG hardware is confirmed. For example, system controller 170 may query acquisition hardware interface 120 of its status. If the status indicates that there is no active connection or attempts to connect to the EEG and/or EOG hardware fail, then an error indicator or a message can be generated for display on user interface 110 as described previously. Alternatively, a sound may be generated to alert the user of a connection problem. These alerts would prompt the user to address the connection problem. If an active communication link between the acquisition hardware interface 120 and the acquisition hardware (i.e. the EEG and/or EOG hardware) is present, then method 200 may proceed to step 230.

As noted previously, EEG electrode impedance may affect the quality of the EEG signal, and therefore, it may affect the ability to reliably perform peak identification and selection of the corresponding EP/ERP waveform. As such, at step 230, impedance measurements are performed to verify whether the measured impedance values are outside of a threshold value or range. For example, for a particular set of EEG electrodes, impedance values below a certain threshold value are preferred. As such, measurements of impedance may be made and then compared against this threshold value. Impedance measurements can be requested for any EEG electrode position in a given array of electrodes. For example, Fz, Cz, Pz and/or EOG electrode at positions hEOG (e.g. "horizontal EOG"—EOG electrode placed beside the subject's eye, near the temple) and vEOG (e.g. "vertical EOG"—EOG electrode placed above the subject's eye). In some embodiments, the EOG and EEG electrodes may be associated with different threshold values. In other embodiments, the EOG and EEG electrodes may be associated with the same threshold value. EEG and EOG electrodes may take any suitable spatial location and configuration to record the signals.

If the measured impedance values of the EEG and/or EOG electrodes are satisfactory (e.g. below the threshold) then the next step of procedure 200 can be performed. However, if the measured impedance values are not satisfactory, then an error indicator or a message can be generated for display on user interface 110. Alternatively, a sound may be generated to alert the user that an impedance issue is present. These alerts would prompt the user to address the impedance issue. For example, electrode impedance can be corrected by doing one or more of the following: applying additional EEG conductive gel to the subject's scalp; re-adjusting the electrode/cap to provide an improved fit; removing excess debris from the subject's hair such as hair gel; abrading the scalp to remove non-conducting skin layers; and cleaning the skin of the scalp with alcohol wipes.

Also noted previously, impedance measurements may be scanned repeatedly to ensure that the impedance of each EEG and/or EOG electrode is within a desired range. Accordingly, system controller 170 may periodically poll (e.g. on demand or at a pre-determined polling frequency) the EEG hardware via the acquisition hardware interface 120 for updated impedance values.

At step 240, a stimulus sequence is received. The stimulus sequence, as described previously, can be a pre-set sequence available for use by EP system 110 or may be customized by the user. For example, the sequence can be selected via user interface 110 and the corresponding output generated by system input/output module 130.

At step 250, the scan is initiated. Upon initiation of the scan, an audio or visual prompt may be generated to indicate to the subject that a scan is about to begin and provide the subject with information about the scanning process and instructions on how to behave during the scan. Following the initial audio or visual prompt, various tones or images of the stimuli sequence may be outputted. Table 1 below shows non-limiting examples of the types of stimuli that may be outputted and corresponding specifications. It should be understood that other stimulus and/or combinations of stimuli can be used in other embodiments of EP system 110 to produce one or more desired EP/ERP waveforms.

TABLE 1

Example of stimulus types and specifications

| Stimulus Type | Specification |
|---|---|
| Standard Tone | A low frequency tone, 50 ms-150 ms in duration |
| Deviant Tone | A high frequency tone, 50 ms-150 ms in duration |
| Semantic Prime Word | A first word in a word pair |
| Semantically Congruent Target Word | The second word in a word pair, semantically congruent with the preceding word (expected condition) |
| Semantically Incongruent Target Word | The second word in a word pair, semantically incongruent with the preceding word (unexpected condition) |
| Contextual Relevant Prime Word | The first word in a word pair, contextually relevant (e.g. if the current day is a Tuesday the contextually relevant prime would be "Tuesday") |

The frequencies of the low frequency standard tone and high frequency deviant tone can be selected such that a minimum tonal difference (i.e. frequency difference) between the two tones is maintained to generate the desired EP/ERP. For example, in one embodiment, the minimum tonal difference is between 5 Hz and 1 kHz. In another embodiment, the minimum tonal difference is between 50 Hz and 800 Hz; In further embodiments, the minimum tonal difference is between 50 Hz and 700 Hz; 50 Hz and 600 Hz; 75 Hz and 550 Hz; 75 Hz and 500 Hz; 80 Hz and 450 Hz; 80 Hz and 400 Hz; 90 Hz and 400 Hz; 95 Hz and Hz 350 Hz; and 100 Hz and 350 Hz. In a particular embodiment, the standard tone is in the range of 700 and 800 Hz and the deviant tone is approximately 300 Hz higher than the standard tone.

During the scan, system controller 170 can record raw data from the EEG and/or EOG electrodes as well as the presence of trigger signals that indicate onset of a stimulus within a stimulus sequence. In some embodiments, multi-channel EEG data are received, each channel corresponding to an electrode in a group of electrodes, each positioned at a suitable spatial location to record the signal. For example, such data can correspond to the Fz, Cz, and Pz channels of the EEG hardware belonging to electrodes embedded in an EEG headset which reside at nominal electrode sites. Data received from the PO7 and Oz channels of the EOG hardware may also be received, the channels being connected to adhesive electrodes at the vEOG/hEOG locations.

In some embodiments, system controller 170 can mark the onset time of each individual stimulus of a particular stimulus sequence that is being outputted. This task can be accomplished by generating a trigger signal to the EEG hardware, for instance, via acquisition hardware interface 120 or any other suitable system component. In some embodiments, the trigger signal may be a generated pulse manifested as a voltage output that can be received and captured by the EEG hardware and provided to EP system 100 along with the EEG data. In other embodiments, the trigger signals may be in the form of trigger codes having different code values. For example, the trigger codes may be hexadecimal values that indicate the type of stimulus being outputted. For example, a first code may be used to denote the start of audio sequence playback, a second code may be used to denote playback of a standard tone, and so on. Table 2 below shows some example of trigger codes that may be used for various types of stimulus outputs. In other embodiments, there may be no trigger signal used and approaches known to those in the art may be used to determine the onset of a stimulus (e.g., by way of synchronization).

TABLE 2

Example Trigger Codes

| Event Description | Serial Trigger Value (hexadecimal) |
|---|---|
| Start of audio sequence playback | 0x0F |
| Standard Tone | 0x01 |
| Deviant Tone | 0x02 |
| Semantic Prime Word | 0x03 |
| Semantically Congruent Target Word | 0x04 |
| Semantically Incongruent Target Word | 0x05 |
| Contextual Prime Word | 0x06 |
| Contextually Relevant Target Word | 0x07 |
| Contextually Irrelevant Target Word | 0x08 |
| End of audio sequence playback | 0x0F |

In some embodiments, a trigger-to-audio (T2A) delay between each trigger signal and the actual playback of a corresponding stimulus can be imposed for all tone-type stimuli. This delay can be imposed, for example, by timing module 140 in respect of a mean T2A value determinable by characterizing EP system 100 prior to initial use by applying methods known to those skilled in the art, which represents the system/hardware delays inherent in EP system 100 and correctable by trigger latency compensation.

At the successful conclusion of a scan, system controller 170 can save the acquired EEG and/or EOG data to data storage 150. For example, system controller 170 may save the collected EEG and/or EOG data in its raw form in a file. The raw EEG data file can contain the data of all the channels recorded by the EEG hardware during the scan, including all available EEG electrodes, battery level, sample number, and a trigger channel indicating the time points at which a stimulus was outputted. The EOG data can be saved in a similar manner.

System controller 170 may also save scan-related metadata in a scan metadata file containing contextual information, scan details, scan date and time, and the name and contents of the stimulus sequence file. As such, in the present embodiment, two output files are generated, comprising one output file for the EEG and/or EOG data and another output file for the metadata. The contents of the two output files may be regarded as the "scan data". In other embodiments, the scan data can be combined into the same data file. The saved scan data may be retrieved subsequently by the user and loaded into data processing module 160 for EP/ERP peak identification and selection, and EP/ERP analysis as described in greater detail below.

In an alternative scanning configuration, the most recently saved scan-related data may be automatically loaded into data processing module 160 for processing and analysis. In another scanning configuration, the scan acquisition and signal processing may be conducted in "real-time" concurrently or substantially concurrently. For example, as a scan session is in progress, acquired EEG and/or EOG data can be saved to data storage 150 and also "streamed" to the data processing module 160 for real-time automated peak identification and selection.

Figure 3:
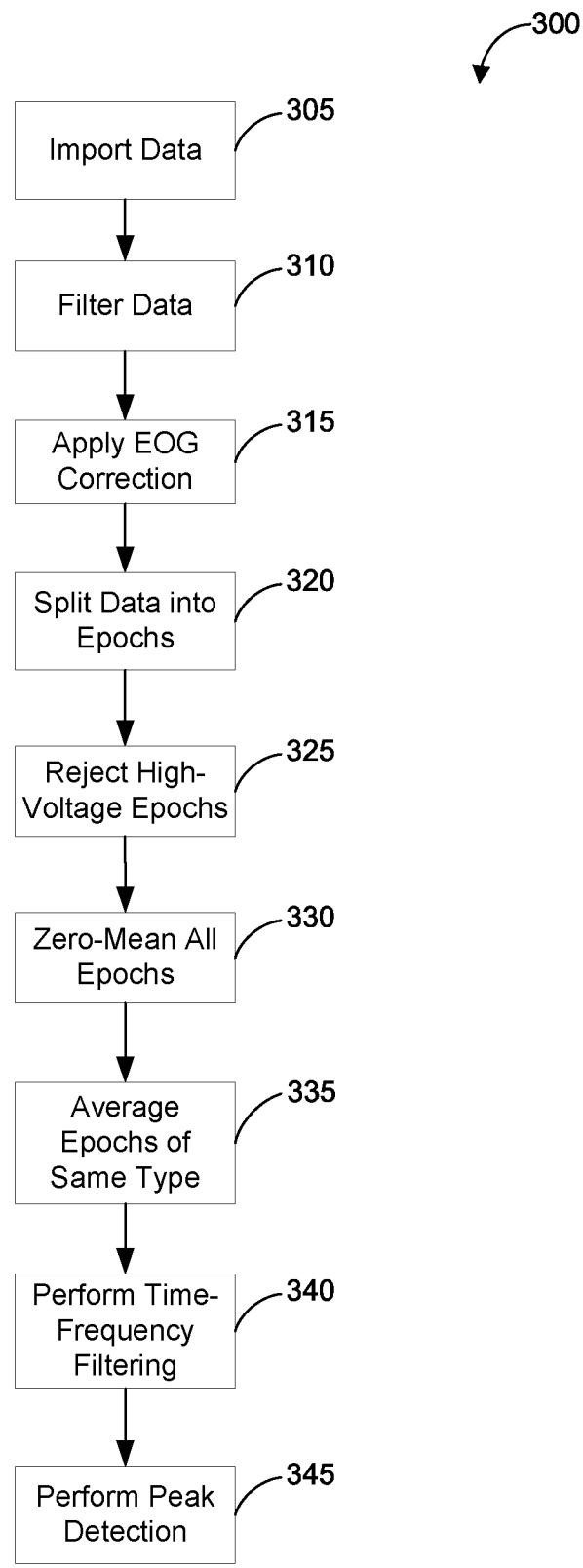
FIG. 3 is a flowchart of a method for processing EEG scan data obtained using the procedure of FIG. 2.

Referring now to FIG. 3, shown therein is a flowchart illustrating a method 300 for processing scan data to enable automatic peak identification and selection of EP/ERP waveforms, and determination of EP/ERP amplitude and latency values. Method 300 may be carried out by the above-described EP system 100 (wherein the data processing steps of the method may be implemented by data processing module 160), a distributed processing resource such as cloud-based computing clusters, or by way of a separate and/or dedicated digital signal processor implemented using techniques known to those in the art, such as, using an application specific integrated circuit (ASIC) or a field programmable gate array (FPGA).

At step 305 of method 300, scan data are imported for analysis. In some embodiments, the scan data corresponding to a completed scan may be retrieved from data storage 150. In this case, user interface 110 is operable to provide a list of data files available for processing (e.g. such data files would not have been marked as having been processed). In some other embodiments, user interface 110 may also provide a suitable presentation that concurrently shows data files that have been processed. In yet other embodiments, user interface 110 may periodically scan data storage 150 to scan for new data files that may be added so as to allow the list of data files of scans to be updated.

The processed data files may be saved in a format that is different from unprocessed data files. For example, raw EEG data (unprocessed) may be in a human readable format (e.g. CSV format) while processed EEG data files may be in a format that is only machine readable (e.g. using binary file formats such as compressible or compressed file formats that can reduce memory use). In some cases, raw and processed EEG data files may contain information that must be kept confidential. As such, raw and processed EEG data files may be encrypted for the purpose of protecting the subject's privacy.

Upon manually or automatically selecting the desired data file for processing, the EEG and/or EOG data and corresponding metadata are "read in" by EP system 100. In some embodiments, the scan data may be verified to assess its validity prior to processing. For example, an error message may be generated if it is determined that the selected data file is corrupted (e.g. missing certain file parameters such as the indication of the number of samples, incorrect file length, and the like), missing from data storage 150, or has already been processed.

At step 310, the imported scan data are filtered to remove higher frequency noise, exclude brain frequencies that are not expected to contribute to the EPs/ERPs of interest, as well as remove low frequency "drift" from the EEG. The filter selected may be any filter suitable for filtering scan data received from the EEG hardware being used. For example, low-pass filters, neural network filters (e.g. autoencoders), and/or moving average filters can be used. In some embodiments, a bandpass filter having a desired pass band may be applied to the raw data of the EEG and/or EOG channels. For instance, the lower-frequency portion of the pass band is operable to remove the higher frequency noise components while the high frequency portion of the pass band is operable to remove the "drift". In some embodiments, the bandpass filter can be implemented using a minimum passband ripple filter such as a Butterworth filter. For example, for EEG and/or EOG channels with a presumed sampling rate of input data of 500 Hz, a fourth order Butterworth filter with a passband between 0.5 Hz to 20 Hz may be suitable. The example parameters can be adjusted accordingly based on different presumed sampling rates and/or noise characteristics.

Figure 4:
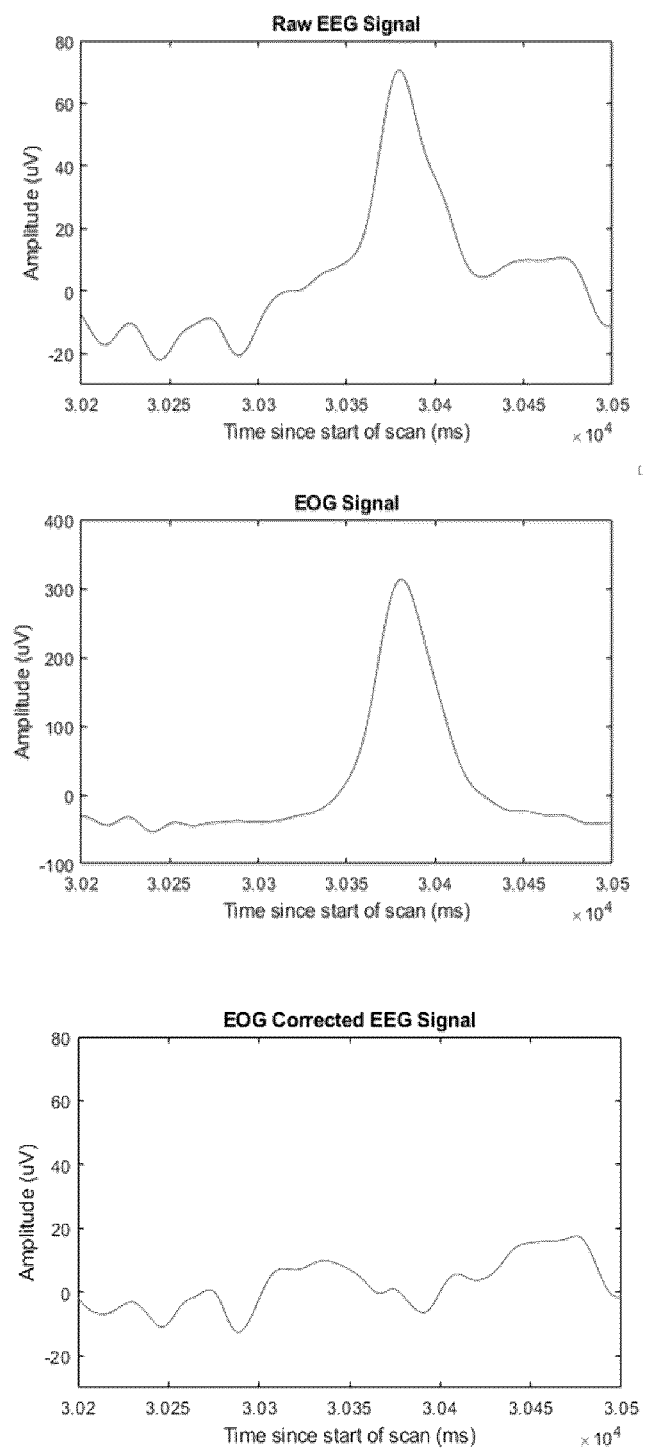
FIG. 4 is a graph of uncorrected and electro-oculogram (EOG)-corrected EEG waveforms and a corresponding EOG waveform used for EOG correction.

At step 315, EOG correction is applied by using EOG data from the EOG hardware to remove artifacts resulting from ocular activity detected during the scan such as eye movement and blinking. Specifically, EOG data can be used as a reference as data from the EEG channels are filtered using an adaptive filter. The EOG data can be automatically captured and saved along with the EEG data for the purposes of EOG correction. For example, a recursive least squares filter with a kernel size of 5 and Forgetting Factor of 0.9999 can be applied. FIG. 4 shows a graph of the EOG signal indicating eye blink, the resulting "contaminated" EEG signal (Fz channel) containing a corresponding blink artifact, and the corrected EEG signal with a reduced artifact. In other embodiments, any other suitable filter can be used, including those that incorporate independent component analysis techniques (ICA) and autoregressive moving-average (exogenous) models (ARMAX).

At step 320, the EOG-corrected EEG data are split into individual epochs using the trigger signals as a timing reference. Each epoch corresponds to a time window immediately surrounding the time at which a stimulus of a stimulus sequence is delivered (the time of delivery of the stimulus being indicated by the associated trigger signal). The size of the epoch can be generally based on physiological factors associated with the EP/ERP of interest. For example the N100, P300, N400 are typically found within this 1 s window. If the epoch interval is too short, the EP/ERP peak may fall outside of the epoch. If the epoch is too long, too much noise may be captured to reliably detect the peaks. The purpose of splitting the EEG data into epochs is to assist in improving peak identification and selection. It is noted that each time a stimulus is delivered, the stimulus elicits a corresponding EP/ERP from the subject, which is recorded by the EEG electrodes. However, the signal-to-noise ratio of such a response is generally too low in a single epoch to enable identification of the EP/ERP waveform. The technique of epoching can be used to "slice" the raw EEG data into segments or "windows" surrounding each stimulus, so that all the epochs of the same stimulus type can be averaged together. This averaging can cause the "noise" component to be averaged to near zero and the "signal" component be reinforced to create a more robust EP/ERP waveform.

Figure 5:
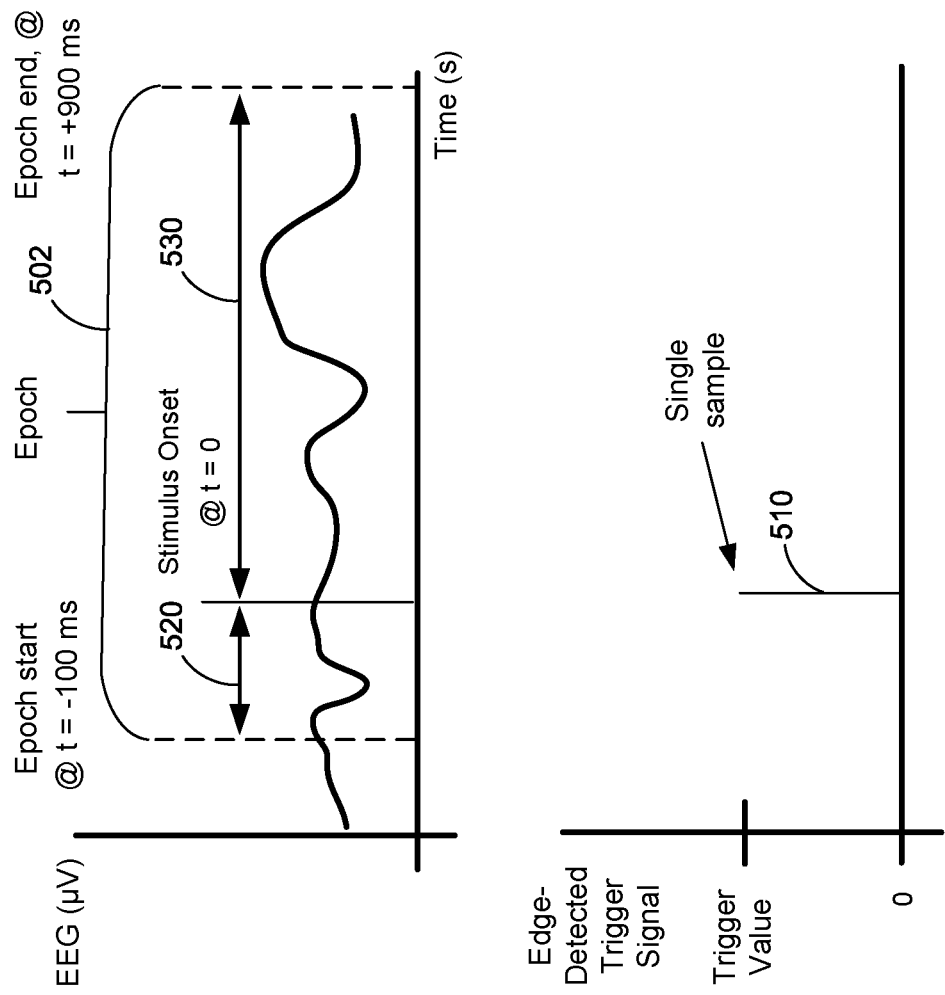
FIG. 5 is a graph of an epoch extracted from EEG data using an associated trigger signal.

In the present embodiment, an epoch can begin 100 ms prior to the onset of stimulus (as indicated by the trigger signal) and may end 900 ms after the onset of stimulus, for an epoch of 1 s in duration or "size". FIG. 5 shows epoch 502 according to the disclosed epoch parameters. The time of the positive edge of trigger signal 510 denotes the start of stimulus. First interval 520 includes the start of epoch 502, which begins 100 ms prior to the onset of stimulus. Second interval 530 includes the end of epoch 502, which terminates 900 ms after the onset of stimulus. However, in other embodiments, epochs of other epoch sizes may be considered. A suitable size of the epoch can be determined by examining various factors. For instance, if further filtering is performed after splitting the data into epochs, a longer epoch may be desirable to avoid blurring filter edge effects at the start or end of the epoch containing the EP/ERP of interest. Further, the time interval between application of stimuli may also affect epoch length, where a greater interval may help avoid blurring EP/ERP responses together. However reducing this interval may also be desirable to obtain shorter scan sessions.

The epochs into which the EOG-corrected EEG data are split may be grouped automatically based on the stimulus type. Epochs associated with stimuli of the same type (e.g. as denoted in Table 1) as indicated by the trigger code (e.g. as denoted in Table 2) may be grouped for averaging as described below.

At step 325, once the EEG data has been split into epochs, epochs in which the EEG voltage exceeds a given threshold value may be rejected. Rejected epochs would be excluded from further processing. High voltages may be attributed to various factors including the EEG hardware being used, or environmental factors such as contact of the electrodes to the subject and the degree of movement of the subject. For example, as shown in FIG. 4, an EOG-contaminated EEG signal can include a spike if 70 µV. As such, other types of movements or environmental factors can contribute to spikes of this magnitude. As such, in one embodiment, the threshold voltage may be set to +/−75 µV. In another embodiment, the threshold may be may be set to +/−100 µV. It may be appreciated that the thresholds may take on different values depending on the configuration of the EEG hardware and the subject being scanned. The threshold for a particular system can therefore be determined by way of calibration or using other suitable methods known to those in the art.

At step 330, following high-voltage epoch rejection, each of the remaining epochs is processed to remove its mean value. Specifically, the mean voltage of a given epoch is subtracted from every data sample of that epoch so that the mean value of the epoch is zero. In some embodiments, the removal of the mean is performed based on a baseline signal captured prior to the application of a stimulus during a baseline period. In some embodiments, this zeroing of the mean value may be performed on a per-channel basis.

At step 335, following mean removal, an average epoch waveform is calculated for epochs corresponding to the same type of stimulus. Given that EPs/ERPs are generally highly variable due to noise, natural physiological variations and other factors, averaging several EP/ERP waveforms allows for the reduction of noise by a factor of $1/\sqrt{n}$, where n is the number of trials. Such averaging produces EP/ERP waveforms that are statistically meaningful as compared to individual EPs/ERPs that are contaminated by noise. In some embodiments, this averaging can be conducted on a per-channel basis.

At step 340, following epoch-averaging, the averaged epoch may be detected in which a further filtering procedure is applied to the EEG data of the averaged epoch. In the present embodiment, the further filtering procedure is performed in the time-frequency domain to further yield optimally smooth EP/ERP waveforms to enable more accurate automated peak identification and selection as described further below. Prior to filtering, the average epoch is transformed into the time-frequency domain using techniques known to those in the art. For example, transformation can be performed by way of using a continuous or discrete wavelet transform. A suitable wavelet type may be applied to perform the transformation. For example, wavelet from one or more different families can be used, including, but not limited to, Haar wavelets, Daubechies wavelets, Biothogonal wavelets, Coiflets wavelets, Morlet wavelets, Symlets wavelets, Mexican Hat wavelets, Meyer wavelets, other real wavelets, complex wavelets, and the like.

Within the time-frequency domain, a time-frequency mask may be applied to the time-frequency representation of the EEG data. For example, the mask may be applied individually to each of the EEG channels. The mask may be used to reject some portions of the time-frequency representation of the averaged epoch while retaining other portions. The configuration of the mask, such as its shape, may be pre-defined for each type of evoked potential based on a normative database. This normative database can constitute a large set (e.g. all or substantially all) of historical scan data and processed waveforms, along with known demographic information of the associated subject such as age, education, medical history. Some or all of the data from this normative database may be used to generate suitable mask configurations. The mask used for application to the time-frequency representation of the EEG data may be automatically selected for the type of EP/ERP elicited. The EP/ERP type may be determinable, for example, from the coded trigger values as described in Table 2 above.

In one example implementation, the mask can be generated using data from the time-frequency representations of one or more pieces of existing EP/ERP data (e.g. using data obtained from past scans that have been saved to the normative database, either with or without demographic information) for a given type of response to determine time-frequency components that are more likely to contain the EP/ERP signal rather than noise. For example, the components can be identified by analyzing the coefficients of the time-frequency representation of the existing EP/ERP data by focusing on time and/or frequency ranges that are likely to include the EP/ERP waveform. Alternatively, the components can be identified by analyzing the power spectrum of the EP/ERP data where power values above a particular threshold (e.g. top 5%, top 10%, top 15% and so on) are likely to include the EP/ERP waveform. Since the time-frequency representation is a two-dimensional quantity, the identified components can serve as coordinates that map to one or more positions of the mask that is to be applied to the average epoch. Each position of the mask is assigned a masking value such that when the mask is applied to the averaged epoch, the mask value at a given position either preserves/augments or attenuates (either partially or completely) a corresponding position of the averaged epoch. Positions of the averaged epoch that are preserved/augmented are expected to contain the EP/ERP signal, while attenuated positions are expected to contain noise components. In one example embodiment, the mask is a binary mask in which positions of the averaged epoch that are intended to be discarded are given a value of 0 (zero) while positions that should be maintained are assigned a value of 1 (one). In another example embodiment, the mask contains a range of values between 0 and 1 such that some components of the averaged epochs are partially discarded, for instance, by using a mask value that is below 1 but greater than 0. The application of the mask allows optimal removal of noise while preserving the signal as much as possible.

In some embodiments, one or more pieces of existing EP/ERP data are chosen so that the contextual information (e.g. demographic information) associated with the averaged epoch is similar to the contextual information associated with the existing EP/ERP data. In other embodiments, the existing EP/ERP data correspond to previous scans of the same subject. In some embodiments, the mask is generated dynamically, at run-time, according to signal properties of the ERP waveform. In some embodiments, all of the scan data in the normative database is considered to generate the resultant mask. However, the mask may not be a good fit for EP/ERP waveforms with unusual shapes. In other embodiments, to account for acquired waveforms that have been determined to contain unusual shapes (e.g. at run-time or otherwise) existing data corresponding to a subset of the normative database having similar waveform shapes can be considered. While a discussion of the normative database above focuses on how it may be used to generate suitable masks, the data within this database may provide insight and guidance with respect to the EP/ERP waveform processing pipeline, including but not limited to, the design of new filters, new filtering techniques, and new peak identification and selection techniques. The historical data set may further be used to generate useful insights into the EP/ERPs themselves. For example, a large data set would enable comparison/correlation between the EPs/ERPs between subjects (e.g. how a subject's N100 latency compares to other people of similar age, and the like).

In some embodiments, this feature extraction process enabling automated peak detection and selection, amplitude and latency measurement can be performed applying machine learning techniques based on the normative database. For instance, human experts may select and label data from the normative database containing relevant peaks of interest. Such data can then be assembled into a training data set used to train (e.g. supervised training) a convolutional neural network (CNN) to perform the same classification task. Once the CNN is trained using data from the normative database, the CNN may be deployed to perform automatic peak identification and selection on EP/ERP data acquired from a scan session.

Once masking is applied in the time-frequency domain to reject desired portions of the time-frequency representation of the averaged epoch, an inverse wavelet transformer is applied to the masked epoch to output a filtered epoch in the time domain.

In some alternative embodiments, time-frequency filtering as described above may be performed on each zero-mean epoch of the same type (e.g. individual/single trials intended to elicit the same type of EP/ERP response from a particular patient), prior to averaging each epoch of the same type (e.g. filtering the epochs after step 330 but before step 335). Averaging of the time-frequency filtered single trial epochs of the same type can further enhance the signal-to-noise ratio (SNR). This approach was described in Fleck-Prediger, Carolyn M., et al. "Point-of-care brain injury evaluation of conscious awareness: wide scale deployment of portable HCS EEG evaluation", Neuroscience of consciousness 2018.1 (2018): niy011.

It may be appreciated that this alternative embodiment may result in improved SNR in the filtered single trial epochs that are subsequently averaged, and may be useful for EP/ERP analysis where the number of trials are limited. However, where many trials are taken or many sets of patient data are to be processed, the computational demand in connection with transforming EEG data for each trial into the time-frequency domain and back may be higher than the embodiment described in FIG. 3 where filtering in the time-frequency domain is performed after averaging each epoch of the same type. In the embodiment of FIG. 3, where epoch averaging is performed before filtering in the time-frequency domain, a single forward transformation and a single inverse transformation is conducted regardless of the number of epochs. By contrast, the alternative embodiment requires performing forward and inverse transformations N times for N epochs.

A greater computational demand translates to a greater burden on system components such as the data processing module 160 and system controller 170. At the design stage, a system engineer may incorporate higher-performance hardware to meet these demands and thereby increase the overall cost of the EP system 100. Additionally, where the EP system 100 is intended to be a mobile/portable system, a larger power supply such as a higher capacity battery may be required to meet the power demands of the processing module 160 tasked with increased computational operations. These power considerations further contribute to the material/hardware costs of the EP system 100 and may increase its overall weight and size. As such, particularly for applications where portability of the EP system 100 is advantageous, or where there are a significant number of sets of patient data to be processed, the embodiment of FIG. 3 is preferred since it provides computational efficiencies.

At step 345, following time-frequency filtering, peak detection is performed on the filtered epochs to identify associated amplitudes and latencies of the EPs/ERPs such as, by way of non-limiting example, the N100, P300, and N400 ERPs. Peak detection may be conducted in a number of ways. For instance, in one non-limiting example, the peak may be determined based on locating a portion of the waveform having peak power. In other implementations, the peak may be detected by identifying a waveform peak, such as a signal voltage extremum. For explanatory purposes, details of peak detection by way of extremum detection are provided below with reference to FIG. 6.

Figure 6:
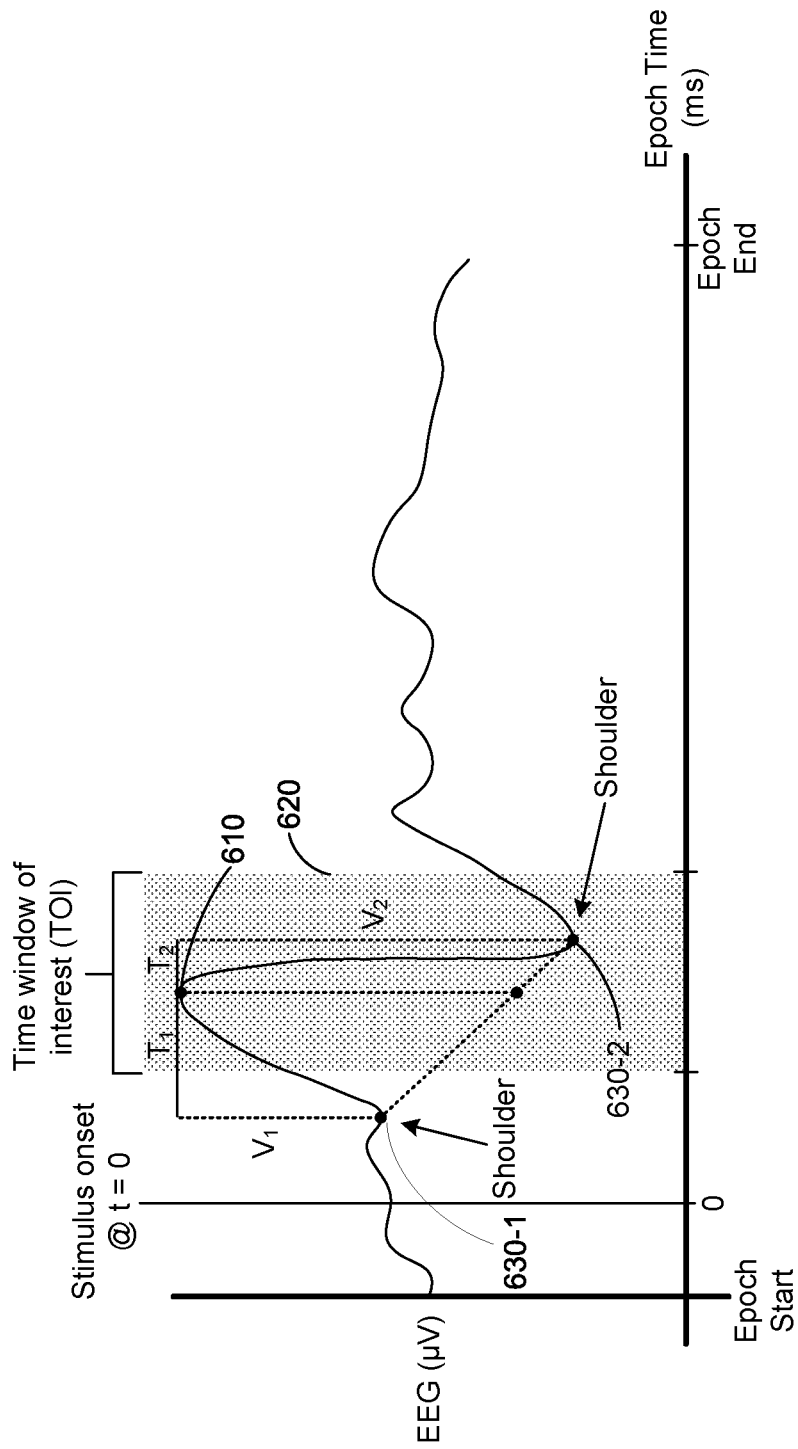
FIG. 6 is a graph of an EP/ERP waveform with a detectable peak.

FIG. 6 shows an example EP/ERP waveform for which the peak and amplitude of the waveform is determinable in an epoch processed using the method described above. As shown in the figure, the amplitude of the peak 610 of the EP/ERP waveform may be defined using the voltage values $V_1$ and $V_2$, and time values $T_1$ and $T_2$ in accordance with the following expression:

$$\text{Amplitude} = (V_1 T_2 + V_2 T_1)/(T_1 + T_2)$$

Shoulders 630-1 and 630-2 (collectively, 630) can be defined as local extrema on either side of peak 610 of the EP/ERP waveform, with opposite concavity to peak 610. First shoulder 630-1 appears $T_1$ seconds before the peak 610, while second shoulder 630-2 appears $T_2$ seconds after peak 610 as shown in FIG. 6. Voltage $V_1$ can be used to denote an amplitude difference between first shoulder 630-1 and peak 610, while voltage $V_2$ can be used to denote an amplitude difference between second shoulder 630-2 and peak 610. Using these quantities, the amplitude of peak 610 can be calculated using the above expression.

Peak 610 of the EP/ERP waveform shown in FIG. 6 can be defined as an extremum of an appropriate polarity (e.g., negative for the N100 and N400 ERPs, and positive for the P300 ERP) within a time window of interest (TOI) 620 applied to the filtered epoch. TOI 620 may be pre-determined intervals that are based on the known characteristics of the various types of EPs/ERPs, such as the typical latency or latency ranges that are generally accepted to be associated with a particular EP/ERP type (the "nominal time"). The rationale is that an EEG response with a peak latency too dissimilar from the nominal time of a particular EP/ERP is by definition not that EP/ERP. The TOI 620 can be defined to be wide enough to capture EPs/ERPs within a reasonable range of natural variability. Therefore, automatic peak identification and selection can be attempted for each EP/ERP within the TOI. Limiting the peak identification and selection to the TOI reduces the likelihood of mistaking other peaks as being the EP/ERP. As such, automated peak and latency detection is made more reliable by using the TOI. Peak 610 may be determined by identifying the extremum within the TOI.

In some embodiments, the TOI can be used in combination with the filtering procedure of method 300 as described above to enable more reliable EP/ERP feature detection. For example, any reduction of SNR that results from filtering the averaged epoch at step 340 relative to the SNR obtainable from applying the alternative embodiment of filtering single trial epochs prior to averaging the filtered epochs may be addressed by limiting the EP/ERP analysis to within the TOI. In other words, the TOI may be used to compensate for any SNR reduction to maintain (or even enhance) reliability of EP/ERP peak identification and latency measurement. This combination allows the EP system 100 to operate more efficiently (e.g. less computationally demanding as described above) without sacrificing performance reliability.

Table 3 below shows non-limiting examples of TOI ranges for various types of ERPs. In other embodiments, other TOI ranges can be used, taking into account the EP/ERP of interest and other factors such as EEG hardware used in the acquisition of the EP/ERP waveforms. In some embodiments, peak detection is attempted for each EP/ERP within the TOI, wherein the TOI reduces the likelihood of erroneous peak detections. If peak detection fails to locate peaks within the specified TOI for the EP/ERP of a given type, then the system can generate an indication that no peak of a given type was found.

TABLE 3

Example Peak Detection Window Limits per ERP

| ERP | Peak Detection Window Limits |
|---|---|
| N100 | $t_{epoch} \in [50, 150]$ ms |
| P300 | $t_{epoch} \in [150, 450]$ ms |
| N400 | $t_{epoch} \in [250, 650]$ ms |

Figure 7:
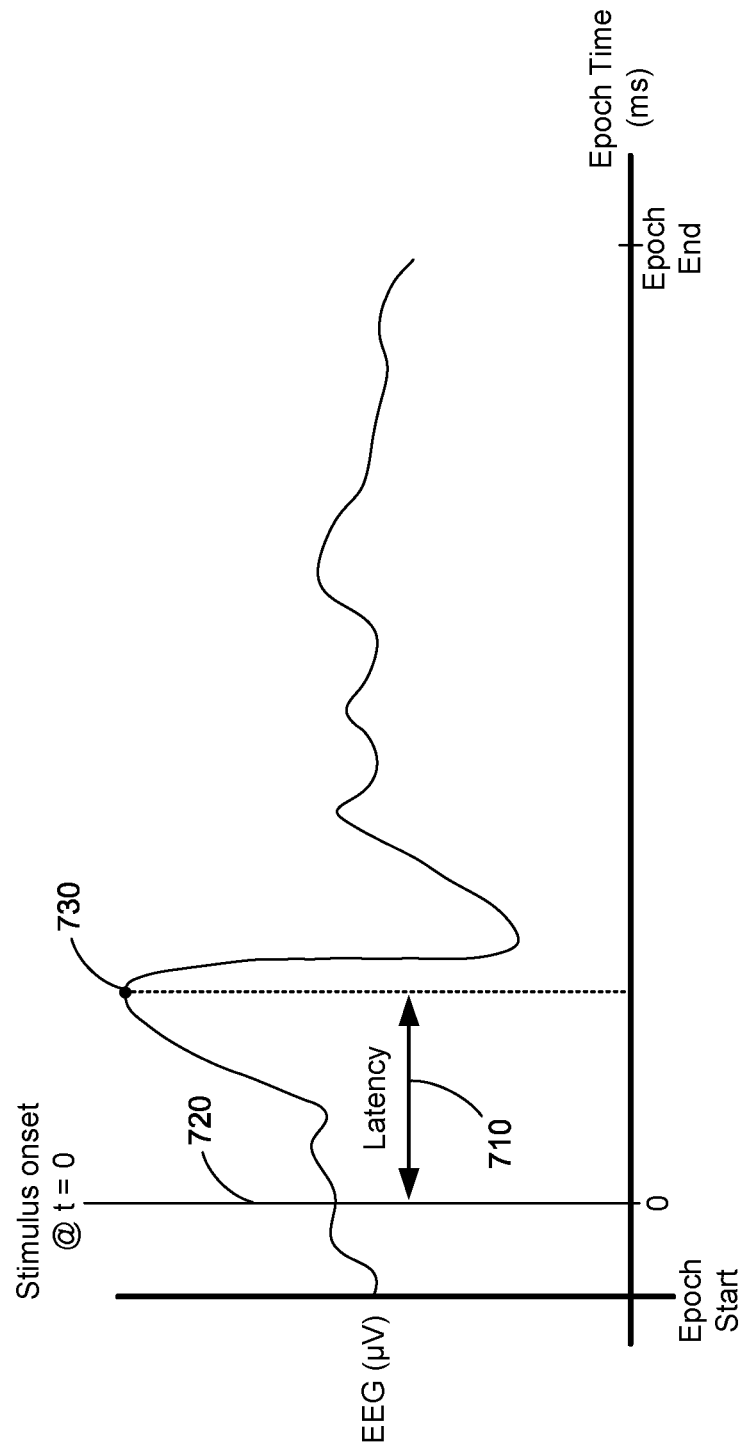
FIG. 7 is a graph of the EP/ERP waveform of FIG. 6 indicating a latency of the detectable peak.

The latency of an EP/ERP waveform can be defined to be the time, relative to stimulus onset (i.e. at time 0), at which the peak occurs. FIG. 7 shows an example EP/ERP waveform with a latency value indicated by reference numeral 710 measured as the time interval between the time of onset of stimulus 720 and the time of the peak 730.

In some embodiments, upon completion of peak detection, a report may be generated summarizing the measured amplitudes and latencies of the various EP/ERP waveforms that were analyzed. FIG. 8 shows an example report that may be generated by ERP system 100 upon completion of a scan. The report, as shown, may be formatted to include a graphical representation of each type of EP/ERP waveform captured in a session with an indicator showing the position of the detected peak, and the corresponding amplitudes and latencies. In some cases, the graphical representation may further superimpose a "standard condition" EP/ERP waveform (i.e. waveform known to be associated with a healthy brain) over the captured EP/ERP waveform to enable visual comparison. Additional data useful for clinicians that are provided in the report may include tabular or graphical views of a subject's scan history for each type of EP/ERP (amplitude and latency). Such data may provide insight into trends that may be indicative of changes to subject's brain health or be used to generate a corresponding brain vital sign. The report may further include comments provided at the time of acquisition to indicate the conditions or events that may have occurred during the scan (e.g. excessive movement of the subject, and the like). Further observations by clinicians may be included in the form of notes with comments to the present scan or past scans. In some embodiments, if peak detection fails to locate peaks within the specified valid time windows, an output may be provided to indicate that no peak was found for a particular EP/ERP waveform.

The examples and corresponding diagrams used herein are for illustrative purposes only. Different configurations and terminology can be used without departing from the principles expressed herein.

Although the invention has been described with reference to certain specific embodiments, various modifications thereof will be apparent to those skilled in the art without departing from the scope of the invention. The scope of the claims should not be limited by the illustrative embodiments set forth in the examples, but should be given the broadest interpretation consistent with the description as a whole.

The invention claimed is:

1. A computer-implemented method to automatically measure an amplitude and a latency of at least one evoked potential (EP) and/or event-related potential (ERP) from electroencephalography (EEG) data, the automation method comprising:
   (a) separating the EEG data into at least one epoch, each epoch containing an EP/ERP waveform associated with at least one type of EP/ERP; and
   (b) upon automatically grouping each epoch according to EP/ERP type, and for each type of EP/ERP having at least one associated epoch, automatically processing the at least one associated epoch by:
      (i) computing, automatically, an average of the at least one associated epoch to output an averaged epoch;
      (ii) upon detecting the outputted average epoch, automatically outputting a time-frequency domain representation of the averaged epoch;
      (iii) automatically applying a time-frequency mask to the time-frequency representation of the averaged epoch to output a masked epoch, wherein the time-frequency mask is automatically selected from a set of time-frequency masks configured to reject at least one time-frequency component of the time-frequency representation of the averaged epoch, wherein the time-frequency mask is predefined for each EP/ERP type, and the time-frequency mask is based on at least one EP/ERP waveform of the same EP/ERP type automatically selected from a normative database;
      (iv) outputting, automatically upon detecting an outputted masked epoch, a filtered epoch corresponding to a time domain representation of the masked epoch;
      (v) automatically selecting a position in the filtered epoch corresponding to an EP/ERP waveform peak; and
      (vi) automatically determining an amplitude value and a latency value of the EP/ERP waveform peak, the latency value corresponding to a time interval between stimulus onset and the EP/ERP waveform peak.

2. The automation method of claim 1 wherein automatically selecting a position in the filtered epoch and determining an amplitude value and a latency value are performed using automatic peak detection.

3. The automation method of claim 1 comprising automatically filtering the EEG data before separating the EEG data into the at least one epoch.

4. The automation method of claim 3 comprising using a bandpass filter to automatically filter the EEG data before separating the EEG data into the at least one epoch.

5. The automation method of claim 1, comprising automatically filtering the EEG data using automatically retrieved electrooculography (EOG) data associated with the EEG data, wherein the EEG data is automatically filtered using the EOG data as a reference signal to automatically remove EEG data artifacts resulting from ocular activity.

6. The automation method of claim 1, comprising automatically excluding an epoch of the at least one associated epoch from computation of the averaged epoch when an EEG voltage within that epoch is determined, automatically, to exceed a voltage threshold value.

7. The automation method of claim 1, comprising, for each of the at least one associated epoch, automatically computing a corresponding mean value from that associated epoch and automatically subtracting the mean value from that associated epoch prior to computing the averaged epoch.

8. The automation method of claim 1, comprising automatically obtaining the time-frequency domain representation by applying a wavelet transform to the averaged epoch and automatically obtaining the filtered epoch by applying an inverse wavelet transform to the masked epoch.

9. The automation method of claim 8, wherein the wavelet transform is automatically selected from one of a Haar wavelet, Daubechies wavelet, Biothogonal wavelet, Coiflets wavelet, Morlet wavelet, Symlets wavelet, Mexican Hat wavelet, and Meyer wavelet.

10. The automation method of claim 1, wherein the EP/ERP waveform peak corresponds to a waveform extremum of the filtered epoch.

11. The automation method of claim 10, wherein the waveform extremum is automatically identified within a time window of interest (TOI) automatically applied to the filtered epoch, based on a pre-defined time interval determined based on a known latency range for a given type of EP/ERP.

12. A computer-implemented method to automatically measure an amplitude and a latency of at least one evoked potential (EP) and/or event-related potential (ERP) from electroencephalography (EEG) data, the automation method comprising:
   (a) separating the EEG data into at least one epoch, each epoch containing an EP/ERP waveform associated with at least one type of EP/ERP; and
   (b) upon automatically grouping each epoch according to EP/ERP type, and for each type of EP/ERP having at least one associated epoch, automatically processing the at least one associated epoch by:
      (i) computing, automatically, an average of the at least one associated epoch to output an averaged epoch;
      (ii) upon detecting the outputted average epoch, automatically outputting a time-frequency domain representation of the averaged epoch;
      (iii) automatically applying a time-frequency mask to the time-frequency representation of the averaged epoch to output a masked epoch, wherein the time-frequency mask is automatically selected from a set of time-frequency masks configured to reject at least one time-frequency component of the time-frequency representation of the averaged epoch, wherein the time-frequency mask for each EP/ERP type of the at least one type of EP/ERP is dynamically generated based on signal properties of the EP/ERP waveform;
      (iv) outputting, automatically upon detecting an outputted masked epoch, a filtered epoch corresponding to a time domain representation of the masked epoch;
      (v) automatically selecting a position in the filtered epoch corresponding to an EP/ERP waveform peak; and
      (vi) automatically determining an amplitude value and a latency value of the EP/ERP waveform peak, the latency value corresponding to a time interval between stimulus onset and the EP/ERP waveform peak.

13. An automated electroencephalography (EEG) system, the automated system comprising:
   (a) an acquisition hardware interface to automatically acquire EEG data by receiving at least one EEG signal from at least one EEG electrode;
   (b) a data storage subsystem to automatically store the EEG data in at least one EEG data file; and
   (c) a data processing module operable to automatically process the EEG data in the at least one EEG data file to automatically measure an amplitude and a latency of at least one evoked response potential (EP/ERP) by:
      (i) separating the EEG data into at least one epoch, each epoch containing an EP/ERP waveform associated with at least one type of EP/ERP; and
      (ii) upon automatically grouping each epoch according to EP/ERP type, and for each type of EP/ERP having at least one associated epoch, automatically processing the at least one associated epoch by:
         A. computing, automatically, an average of the at least one associated epoch to output an averaged epoch;
         B. upon detecting the outputted average epoch, automatically outputting a time-frequency domain representation of the averaged epoch;
         C. automatically applying a time-frequency mask to the time-frequency representation of the averaged epoch to output a masked epoch, wherein the mask is automatically selected from a set of time-frequency masks configured to reject at least one time-frequency component of the time-frequency representation of the averaged epoch, wherein the time-frequency mask is predefined for each EP/ERP type, and the time-frequency mask is based on at least one EP/ERP waveform of the same EP/ERP type automatically selected from a normative database;
         D. outputting, automatically upon detecting an outputted masked epoch, a filtered epoch corresponding to a time domain representation of the masked epoch;
         E. automatically selecting a position in the filtered epoch corresponding to an EP/ERP waveform peak; and
         F. automatically determining an amplitude value and a latency value of the EP/ERP waveform peak, the latency value corresponding to a time interval between stimulus onset and the EP/ERP waveform peak.

14. The automated system of claim 13 wherein the data processing module is configured to automatically select a position in the filtered epoch and determine an amplitude value and a latency value using automatic peak detection.

15. The automated system of claim 13, wherein the data processing module is configured to automatically filter the EEG data before separating the EEG data into the at least one epoch.

16. The system of claim 15 wherein the EEG data is automatically filtered using a bandpass filter.

17. The automated system of claim 13, wherein the acquisition hardware interface is further operable to automatically acquire electrooculography (EOG) data associated with the EEG data by automatically receiving at least one EOG signal from at least one EOG electrode, and wherein the EEG data are automatically filtered using the EOG data as a reference signal to automatically remove EEG data artifacts resulting from ocular activity.

18. The automated system of claim 13, wherein an epoch in the at least one associated epoch is automatically excluded from computation of the averaged epoch when an EEG voltage within that epoch is determined, automatically, to exceed a voltage threshold value.

19. The automated system of claim 13, wherein, for each of the at least one associated epoch, a corresponding mean value is automatically computed from that associated epoch and the mean value is automatically subtracted from that associated epoch prior to computing the averaged epoch.

20. The automated system of claim 13, wherein the time-frequency domain representation is automatically obtained by applying a wavelet transform to the averaged epoch and the filtered epoch is automatically obtained by applying an inverse wavelet transform to the masked epoch.

21. The automated system of claim 20, wherein the wavelet transform is automatically selected from one or more of: a Haar wavelet, Daubechies wavelet, Biothogonal wavelet, Coiflets wavelet, Morlet wavelet, Symlets wavelet, Mexican Hat wavelet, and Meyer wavelet.

22. The automated system of claim 13, wherein the ERP waveform peak corresponds to a waveform extremum of the filtered epoch.

23. The automated system of claim 22, wherein the waveform extremum is automatically identified within a time window of interest (TOI) automatically applied to the filtered epoch, based a pre-defined time interval determined based on a known latency range for a given type of ERP.

24. An automated electroencephalography (EEG) system, the automated system comprising:
   (a) an acquisition hardware interface to automatically acquire EEG data by receiving at least one EEG signal from at least one EEG electrode;
   (b) a data storage subsystem to automatically store the EEG data in at least one EEG data file; and
   (c) a data processing module operable to automatically process the EEG data in the at least one EEG data file to automatically measure an amplitude and a latency of at least one evoked response potential (EP/ERP) by:
      (i) separating the EEG data into at least one epoch, each epoch containing an EP/ERP waveform associated with at least one type of EP/ERP; and
      (ii) upon automatically grouping each epoch according to EP/ERP type, and for each type of EP/ERP having at least one associated epoch, automatically processing the at least one associated epoch by:
         A. computing, automatically, an average of the at least one associated epoch to output an averaged epoch;
         B. upon detecting the outputted average epoch, automatically outputting a time-frequency domain representation of the averaged epoch;
         C. automatically applying a time-frequency mask to the time-frequency representation of the averaged epoch to output a masked epoch, wherein the mask is automatically selected from a set of time-frequency masks configured to reject at least one time-frequency component of the time-frequency representation of the averaged epoch, wherein the time-frequency mask for each ERP type of the at least one type of ERP is dynamically generated based on signal properties of the ERP waveform;

D. outputting, automatically upon detecting an outputted masked epoch, a filtered epoch corresponding to a time domain representation of the masked epoch;
E. automatically selecting a position in the filtered epoch corresponding to an EP/ERP waveform peak; and
F. automatically determining an amplitude value and a latency value of the EP/ERP waveform peak, the latency value corresponding to a time interval between stimulus onset and the EP/ERP waveform peak.

* * * * *